United States Patent [19]

Yamaguchi et al.

[11] Patent Number: 4,769,463

[45] Date of Patent: Sep. 6, 1988

[54] 2,6-BIS(AMINOPHENOXY)PYRIDINE AND METHOD OF PREPARING THE SAME

[75] Inventors: Keizaburo Yamaguchi, Kawasaki; Kenichi Sugimoto, Yokohama; Yukihiro Yoshikawa, Zushi; Yoshimitsu Tanabe, Yokohama; Akihiro Yamaguchi, Kamakura, all of Japan

[73] Assignee: Mitsui Toatsu Chemicals, Inc., Tokyo, Japan

[21] Appl. No.: 24,461

[22] Filed: Mar. 11, 1987

[51] Int. Cl.$^4$ .......................................... C07D 213/64
[52] U.S. Cl. ..................................... 546/296; 546/300
[58] Field of Search ........................................ 546/296

[56] References Cited

U.S. PATENT DOCUMENTS 4,222,962  9/1980  Pellegrini, Jr. ..................... 564/430

FOREIGN PATENT DOCUMENTS 2462112  3/1976  Fed. Rep. of Germany ...... 528/322

OTHER PUBLICATIONS

Chem. Abstracts, vol. 107(21), Abst. No. 198, 105g, Nov. 23, 1987.
Helv. Chim. Acta, 51, 971 (1968).
Great Organic Chemistry, Series 16, p. 20, by Asakura Bookstore.
Oxydation and Reduction, [II], Experimental Chemistry Court, vol. 15, by Maruzen Comp.

*Primary Examiner*—Alan L. Rotman
*Attorney, Agent, or Firm*—Fisher, Christen & Sabol

[57] ABSTRACT

Noval diamines, 2,6-bis(3-aminophenoxy)pyridine and 2,6-bis-(4-aminophenoxy)pyridine, are provided and the method of their preparation is disclosed. These diamines are useful as raw materials for polyimide.

These diamines can be prepared by the reaction of 2,6-dichloropyridine or 2,6-dibromopyridine with 3-aminophenol or 4-aminophenol in aprotic polar solvents in the presence of bases.

Besides, 2,6-bis(3-aminophenoxy)pyridine can also be prepared by the reaction of 2,6-dicholorpyridine or 2,6-dibromopyridine with 3-nitrophenol, followed by reducing resultant 2,6-bis(3-nitrophenoxy)pyridine.

1 Claim, No Drawings

2,6-BIS(AMINOPHENOXY)PYRIDINE AND METHOD OF PREPARING THE SAME

BACKGROUND OF THE INVENTION

This invention relates to 2,6-bis(3- or 4-aminophenoxy)pyridine having the following formula(I):

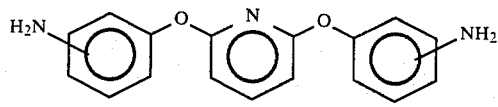

(where one amino group is located in each benzene ring either at both meta- or both para- position to each oxy radical) and the method of its preparation.

More particularly, this invention relates to the above mentioned diamine (I) which is used as the material for polyimide resin having remarkably improved processing ability and adhesive strength, and the method for preparing the same.

2,6-Bis(3- or 4-aminophenoxy)pyridine has never been prepared and its use has been unknown. The derivative has been prepared for the first time by the present inventors and found to be useful for the material of polyimide. The derivative can also be applied for the raw material of polyamide and bismaleimide as well as a hardener of epoxy resin.

Polyimide has excellent properties and yet has a drawback of being difficult to process.

The present inventors investigated extensively in order to improve these drawbacks. As a result, enhancement of flexibility and easiness of processing has been found to be achieved without reduction in high-temperature stability by eliminating the linearity of polyimide structure and increasing the unit of ether linkage.

Polyimide derived from diamine derivatives having plural ether linkages at the meta-positions is regarded as the chemical structure meeting these conditions.

1,3-Bis(3-aminophenoxy)benzene has been traditionally known as a diamine derivative having such structure. Polyimide derived from this derivative has been also known to have properties of high strength and outstanding high-temperature stability.

The diamine derivative, however, has also been known to be difficult in preparation. Several processes have been known, for example; a method of preparation by condensing resorcinol with 1-bromo-3-nitrobenzene and reducing the resultant intermediate (German Pat. No. 2,462,112) and a method of preparation by the condensation of 3-aminophenol with 1,3-dibromobenzene [Helv. Chim. Acta., 51, 971(1968); U.S. Pat. No. 4,222,962]. In these methods, the diamine is prepared by using relatively low reactive materials such as 1-bromo-3-nitrobenzene and 1,3-dibromobenzene, copper-based catalysts and a large amount of solvents such as pyridine which is difficult to handle because of odor. Consequently, the yield becomes low and a great deal of expenditure and labor is consumed for the disposal of wastes and solvents, which renders the diamine derivative very expensive.

As mentioned above, polyimide derived from 1,3-bis(3-aminophenoxy)benzene has a drawback of high price, in spite of usefulness due to excellent flexibility. Therefore supply of cheap resin having good processability and high-temperature stability has been desired to achieve by overcoming these difficulties.

Furthermore, polyimide having nitrogen containing heterocyclic rings in its structure together with high-strength, high-temperature stability and other special properties has been quite unknown. The development of such resin, and thus that of derivatives for use as the raw materials have been deeply desired.

SUMMARY OF THE INVENTION

The present inventors have investigated extensively in order to solve above mentioned problems. As a result of examination on a variety of meta substituted aromatic dihalides, above mentioned objects have been found to be achieved by the diamine derivatives which are highly reactive, stable in a thermal or other atmosphere and capable of being derived from 2,6-dihalogenopyridine.

That is, one of the present invention is 2,6-bis(3- or 4-aminophenoxy)pyridine having the following formula (I):

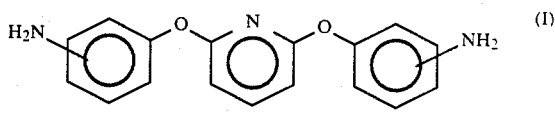

(where one amino group is located in each benzene ring either at both meta- or both para- position to each oxy radical).

Another of the present invention is a method of preparing 2,6-bis(3- or 4-aminophenoxy)pyridine which comprises reacting 2,6-dihalogenopyridine with 3- or 4-aminophenol in an aprotic polar solvent in the presence of a base.

Still another of the present invention is a method of preparing 2,6-bis(3-aminophenoxy)pyridine which comprises reacting 2,6-dihalogenopyridine with 3-nitrophenol in an aprotic polar solvent in the presence of a base and reducing resultant 2,6-bis(3-nitrophenoxy)pyridine.

DETAILED DESCRIPTION OF THE INVENTION 2,6-Bis(3- or 4-aminophenoxy)pyridine of this invention is a nitrogen containing diamine derivative having a pyridine ring in the center of its molecule, two ether linkages at meta position of the pyridine ring and two amino groups on both ends of the molecule.

Therefore, molecular linearity is eliminated in polyimide obtained, for example, by reacting 2,6-bis(3-aminophenoxy)pyridine with pyromellitic dianhydride or 3,3',4,4'-benzophenonetetracarboxylic dianhydride. Thus such polyimide has a glass transition temperature of 216° C. and 206° C. respectively, an ability for easy processing and a very high level of 5% weight decrease temperature in air of above 500° C.

Besides polyimide derived from 2,6-bis(4-aminophenoxy)pyridine of this invention also has similar properties of high strength and excellent high-temperature stability. For example, a tough film can be obtained from polyimide prepared by reacting with benzophenonetetracarboxylic dianhydride. The film has a 5% weight decrease temperature in air of above 500° C. and exhibits an outstanding high-temperature stability.

In addition, polyimide derived from diamines of this invention is found to have a strong adhesive strength to metals or ceramics as an effect of nitrogen atoms in the molecule. Accordingly, such polyimide can be widely applied for other uses than the molding materials, that is, high-temperature adhesives for various metals and ceramics.

Moreover, such polyimide enhances coordination ability to metal ions and thus can be expected to have an improvement in the adhesive strength to metals and electrical conductivity by doping with metal ions.

As stated above, polyimide derived from 2,6-bis(3- or 4-aminophenoxy)pyridine demonstrates excellent properties and thus above mentioned diamine raw materials have proved to be very useful.

2,6-Bis(3-aminophenoxy)pyridine of this invention can be obtained by reacting 2,6-dihalogenopyridine with 3-aminophenol. 2,6-Bis(4-aminophenoxy)pyridine of this invention can be obtained by reacting 2,6-dihalogenopyridine with 4-aminophenol. In any case, the reaction is carried out in an aprotic solvent in the presence of a base.

2,6-Dihalogenopyridine of this invention includes 2,6-difluoropyridine, 2,6-dichloropyridine, 2,6-dibromopyridine and 2,6-diiodopyridine. Among these pyridine derivatives, preferably used are 2,6-dichloropyridine and 2,6-dibromopyridine and most preferably used is technically inexpensive 2,6-dichloropyridine.

These 2,6-dihalogenopyridines are prepared by the halogenation of pyridine [Great Organic Chemistry Series, 16, 20 (published by Asakura Bookstore)].

The quantity of 3-aminophenol used is from 2 to 5 moles and preferably from 2.1 to 3 moles based on 1 mol of 2,6-dihalogenopyridine.

The base for use in the method of this invention is specifically hydroxides, carbonates, hydrogen carbonates and alkoxides of alkali metals, and includes, for example, potassium hydroxide, sodium hydroxide, lithium hydroxide, potassium carbonate, sodium carbonate, lithium carbonate, potassium hydrogen carbonate, sodium hydrogen carbonate, potassium ethoxide, potassium isopropoxide, sodium methoxide, sodium ethoxide and lithium ethoxide. Technically, hydroxides and carbonates of potassium and sodium are used. The base is used, of course, alone or in combination of two and more.

The base used is sufficiently in a quantity of one equivalent and more, preferably from 1 to 1.5 equivalent based on 3- or 4-aminophenol.

The aprotic polar solvent is used as the solvent for proceeding with the reaction in the method of this invention.

The aprotic polar solvent includes, for example, N-methylformamide, N,N-dimethylformamide, N,N-dimethylacetamide, 1-methyl-2-pyrroladinone, 1,3-dimethyl-2-pyrrolidinone, 1,3-dimethyl-2-imidazolidinone, phosphoric hexamethyltriamide, dimethyl sulfoxide, dimethyl sulfone and sulfolane.

The quantity for use of the solvent is not restricted in particular and from 1 to 10 times by weight of the raw materials are normally enough.

Reaction accelerators which may be added in this reaction include quaternary ammonium salts, quaternary phosphates, macro cyclic polyethers such as crown ether, nitrogen containing macrocyclic polyethers such as cryptate, nitrogen containing chain polyethers, phase transfer catalysts such as polyethylene glycols and their alkyl ethers, copper powder and copper salts.

As a general embodiment, following procedures are conducted for preparing 2,6-bis(3- or 4-aminophenoxy)-pyridine by use of above mentioned raw materials and reactants. The prescribed amount of 3- or 4-aminophenol, the base and the solvent were charged, 3- or 4-aminophenol is converted to its alkali metal salt and 2,6-dihalogenopyridine is added in order to carry out the reaction. In an alternative procedure, all of the materials containing 2,6-dihalogenopyridine are simultaneously charged, and the mixture is elevated its temperature and reacted as it is. Either procedure may be conducted. The procedures, of course, are not restricted in particular, and may be optionally conducted by other embodiments.

As a method of removing water generated in the reaction system, there is a process of gradually discharging water from the system during the reaction by ventilating inert gas such as nitrogen. Generally, however, a small amount of benzene, toluene, xylene or chlorobenzene is often added to the reaction system and evolved water is azeotropically removed out of the system.

When 3-aminophenol is used, the reaction temperature is in the range of 120°–140° C. and preferably 140°–200° C. In the case of 4-aminophenol, the reaction temperature is in the range of 80°–240° C., and preferably 120°–200° C.

After completing the reaction, the reaction mixture is concentrated, or as it is, and poured into water to obtain the product.

The end point of the reaction can be determined by observing the decrease of unreacted intermediates with thin layer chromatogrsphy or high-speed liquid chromatography.

2,6-Bis(3-aminophenoxy)pyridine can also be prepared by an alternative method from 2,6-dihalogenopyridine and 3-nitrophenol.

That is, 2,6-bis(3-aminophenoxy)pyridine is prepared by reacting 2,6-dihalogenopyridine with 3-nitrophenol in the aprotic polar solvent in the presence of the base and reducing the resultant 2,6-bis(3-nitrophenoxy)pyridine intermediate.

2,6-Dihalogenopyridine in use for the first step of this invention includes, 2,6-difluoropyridine, 2,6-dichloropyridine, 2,6-dibromopyridine and 2,6-diiodopyridine. Among these pyridine derivatives, preferably used are 2,6-dichloropyridine and 2,6-dibromopyridine and most preferably used is technically inexpensive 2,6-dichloropyridine.

3-Nitrophenol is used in a quantity of 2–5 mols, preferably 2.1–3 moles per mol of 2,6-dihalogenopyridine.

The base used in this method is the same as in the aforesaid method of reacting 2,6-dihalogenopyridine with aminophenols.

The quantity of the base used is sufficiently one equivalent and more, preferably 1–1.5 equivalent based on 3-nitrophenol.

The aprotic polar solvent in use for this method is the same as in the aforesaid method. The quantity is not restricted in particular and sufficiently in the range of 1–10 times by weight based on the total weight of raw materials.

Besides in this reaction, reaction accelerators may also be used. The accelerators include quaternary ammonium salts, quaternary phosphates, macrocyclic polyethers such as crown ether, nitrogen containing macrocyclic polyethers such as cryptate, nitrogen containing chain polyethers, phase transfer catalysts such as polyethylene glycols and their alkyl ethers, copper powder and copper salts.

As a general embodiment, following procedures are conducted for preparing dinitro intermediates by use of above mentioned raw materials and reactants.

The prescribed amount of 3-nitrophenol, the base and the solvent were charged, 3-nitrophenol is converted to its alkali metal salt and 2,6-dihalogenopyridine is added in order to carry out the reaction. In an alternative procedure, all of the materials containing 2,6-dihalogenopyridine are simultaneously charged, and the mixture is elevated its temperature and reacted as it is. Either procedure may be conducted. The procedures, of course, are not restricted in particular, and may be optionally conducted by other embodiments.

As a method of removing water generated in the reaction system, there is a process of gradually discharging water from the system during the reaction by ventilating inert gas such as nitrogen. Generally, however, a small amount of benzene, toluene, xylene or chlorobenzene is often added to the reaction system and evolved water is azeotropically removed out of the system.

The reaction temperature is in the range of 120°–240° C., preferably in the range of 140°–200° C.

After completing the reaction, the reaction mixture is concentrated, or as it is, and poured into water to obtain the product.

The end point of the reaction can be determined by observing the decrease of unreacted intermediates with thin layer chromatography or high-speed liquid chromatography.

In the next step, the second reaction of reducing 2,6-bis(3-nitrophenoxy)pyridine in order to prepare the desired product, 2,6-bis(3-aminophenoxy)pyridine, can be normally conducted by applying the process of reducing nitro group to amino group [described in, for example, Experimental Chemistry Course, vol 15, Oxydation and Reduction, [II], Published by Maruzen (1977)]. Catalytic reduction or hydrazine reduction, however, is prefered technically.

In the catalytic reduction of nitro group, may be employed metallic catalysts which are generally used in the catalytic reduction. The metallic catalysts include, for example, nickel, palladium, platinum, rhodium, ruthenium, cobalt and copper. The palladium catalyst is preferably used technically. Although these catalysts may be used in the metallic state, they are normally employed by loading on the surface of carrier, such as carbon, barium sulfate, silica gel, alumina and cellite. In addition, nickel, cobalt and copper are also applied as Raney catalysts.

The quantity of catalysts is not restricted in particular, and in the range, converted into metal, of 0.01–10% by weight based on 2,6-bis(3-nitrophenoxy)pyridine. It ranges normally 2–8% by weight when used in the form of metal, and 0.1–5% by weight when loaded on the carrier.

The solvent for use in the reaction is not restricted in particular so long as it is inert in the reaction. Preferably used are, for example, alcohols such as methanol, ethanol and isopropyl alcohol; glycols such as ethylene glycol and propylene glycol; ethers such as ethyl ether, dioxane, tetrahydrofuran, 2-methoxyethanol and 2-ethoxyethanol. Optionally used are aliphatic hydrocarbons such as hexane and cyclohexane; aromatic hydrocarbons such as benzene, toluene and xylene; esters such as ethyl acetate and butyl acetate; halogenated hydrocarbons such as dichloromethane, chloroform, carbon tetrachloride, 1,2-dichloroethane, 1,1,2-trichloroethane and tetrachloroethane; and N,N-dimethylformamide.

When a water immiscible solvent is used in the reaction, slow rate of reaction can be accelerated by addition of the generally used phase transfer catalysts such as quaternary ammonium salts and quaternary phosphonium salts.

The solvent is satisfactorily used in the quantity enough to disperse or completely dissolve the raw materials. The quantity is not restricted in particular and normally sufficient in the range of 0.5–10 times by weight of raw materials.

The reaction temperature is not restricted in particular and generally in the range of 20°–200° C., preferably in the range of 20°–100° C. in particular. Besides the reaction pressure is normally around from ambient to 50 $kg/cm^2$ G.

In proceeding with the reaction, the raw materials are normally dissolved or suspended in the solvent, followed by adding the catalysts and introducing hydrogen with stirring at a prescribed temperature in order to carry out the reducing reaction. The end point of the reaction can be determined either by the amount of hydrogen absorbed or by thin layer chromatography as well as high-speed liquid chromatography.

On the other hand, when the reduction by hydrazine is conducted, hydrazine is normally used in the quantity of a little excess to the theoretical amount, preferably in the range of 1.2–2 times.

The catalysts used for the hydrazine reduction are above mentioned metallic catalysts which are generally employed for the catalytic reduction. Technically prefered among these catalysts is palladium/carbon, platinum/carbon or a ferric chloride catalyst adsorbed on active carbon. The quantity of catalysts is not restricted in particular and normally in the range, converted into metal, of 0.01–30% by weight based on the raw material, 2,6-bis(3-nitrophenoxy)pyridine.

The solvent used for the hydrazine reduction is the same as in the catalytic reduction.

The reaction temperature is not restricted in particular, and generally in the range of 20°–150° C., preferably in the range of 40°–100° C. in particular.

In proceeding with the reaction, the raw materials are normally dissolved or suspended in the solvent, followed by adding the catalysts and dropwise introducing hydrazine with stirring at a prescribed temperature in order to carry out the reducing reaction. The end point of the reaction can be determined by thin layer chromatography or high-speed liquid chromatography.

After completing the reaction, the reaction mixture is hot-filtered to remove the catalysts and, if required, the solvent is distilled off.

The desired product, crude 2,6-bis(3-aminophenoxy)-pyridine, is obtained. The crude product can be purified by recrystallization or isolation as hydrochloride.

EXAMPLES

The present invention will be hereinafter illustrated further in detail with respect to Examples and Reference examples.

EXAMPLE 1

A 200 ml flask equipped with a stirrer and a water separator was charged with 22.4 grams (0.205 mol) of 3-aminophenol, 12.8 grams (0.22 mol) of flaked 96% potassium hydroxide, 100 ml of dimethyl sulfoxide and 10 ml of toluene. The mixture was raised its temperature with stirring under ventilation of nitrogen. Water in the reaction system was removed by the water separator under reflux of toluene.

In the next step, 14.8 grams (0.1 mol) of 2,6-dichloropyridine was added to the reaction mixture after lowering the internal temperature to below 100° C. The temperature was raised again and the internal temperature was maintained at 150°–160° C. The reaction was completed after conducting for 8 hours at this temperature. The resultant mixture was cooled and poured into 500 ml of water. The separated brown mass was filtered, washed with water and dried to give 28.2 grams (96.2% yield) of 2,6-bis(3-aminophenoxy)pyridine. Crude 2,6-bis(3-aminophenoxy)pyridine was recrystallized twice from isopropyl alcohol to obtain pure product as white needles having a melting point of 119°–120° C. The results of elementary analysis and mass spectrum are as follows:

| Elementary analysis ($C_{17}H_{15}N_3O_2$) | | | |
|---|---|---|---|
| | C | H | N |
| Calculated (%) | 69.61 | 5.15 | 14.33 |
| Found (%) | 69.86 | 5.10 | 14.28 |

MS Spectrum
(M/e)
M⁺ 293, 185, 157, 92, 65

EXAMPLE 2

A 200 ml flask equipped with a stirrer and a water separator was charged with 22.4 grams (0.205 mol) of 4-aminophenol, 12.8 grams (0.22 mol) of flaked 96% potassium hydroxide, 100 ml of dimethyl sulfoxide and 10 ml of toluene. The mixture was raised its temperature with stirring under ventilation of nitrogen. Water in the reaction system was removed by the water separator under reflux of toluene.

In the next step, 14.8 grams (0.1 mol) of 2,6-dichloropyridine was added to the reaction mixture after lowering the internal temperature to 100° C. The temperature was raised again and the internal temperature was maintained at 135°–145° C. The reaction was completed after conducting for 8 hours at this temperature. The resultant mixture was cooled and poured into 500 ml of water. The separated brown mass was filtered, washed with water and dried to give 27.5 grams (93.9% yield) of 2,6-bis(4-aminophenoxy)pyridine. Crude 2,6-bis(4-aminophenoxy)pyridine was recrystallized twice from ethanol to obtain pure product as white needles having a melting point of 152.5°–154.5° C. The results of elementary analysis and mass spectrum are as follows:

| Elementary analysis ($C_{17}H_{15}N_3O_2$) | | | |
|---|---|---|---|
| | C | H | N |
| Calculated (%) | 69.61 | 5.15 | 14.33 |
| Found (%) | 69.51 | 5.20 | 14.37 |

MS Spectrum
(M/e)
M⁺ 293, 185, 157, 92, 65

EXAMPLE 3

A 200 ml flask equipped with a stirrer was charged with 14.8 grams (0.1 mol) of 2,6-dichloropyridine, 22.9 grams (0.21 mol) of 3-amiophenol, 20.7 grams (0.15 mol) of anhydrous potassium carbonate and 115 ml of 1,3-dimethyl-2-imidazolidinone. The mixture was reacted for 14 hours at an internal temperature of 180°–190° C. with stirring under ventilation of nitrogen.

After completing the reaction, the resultant reaction mixture was filtered to remove inorganic salt and concentrated under reduced pressure to recover most of the solvent. The residual brown oil was dissolved in a dilute hydrochloric acid solution consisting of 15.6 grams of 35% aqueous hydrochloric acid and 84 grams of water. The solution thus obtained was decolorized by adding active carbon and filtered. The filtrate was added with 100 ml of isopropyl alcohol and neutralized with aqueous ammonia. The separated white needles were filtered and dried to obtain 26.2 grams (89.4% yield) of 2,6-bis(3-aminophenoxy)pyridine having a melting point of 118.5°–119.5° C.

EXAMPLE 4

The reaction and purification procedures of Example 3 were repeated except 4-aminophenol was used in place of 3-aminophenol and the reaction was conducted for 8 hours. 1,3-Bis(4-aminophenoxy)pyridine thus obtained was 27.2 grams (92.8% yield) having a melting point of 152°–154° C.

EXAMPLE 5

In Example 1, 23.7 grams (0.1 mol) of 2,6-dibromopyridine and 9.2 grams (0.22 mol) of flaked 96% sodium hydroxide were used as raw materials, 100 ml of N,N-dimethylformamide was used as a solvent, and the reaction was carried out at a temperature of 140°–150° C. for 10 hours. Other reaction conditions conducted were the same as in Example 1.

Crude 2,6-bis(3-aminophenoxy)pyridine thus obtained was recrystallized from isopropyl alcohol to give 23.9 grams (81.6% yield) of pure product having a melting point of 118.5°–120° C.

EXAMPLE 6

In Example 2, 23.7 grams (0.1 mol) of 2,6-dibromopyridine and 9.2 grams (0.22 mol) of flaked 96% sodium hydroxide were used as raw materials, 100 ml of N,N-dimethylformamide was used as a solvent, and the reaction was carried out at a temperature of 115°–125° C. for 10 hours. Other reaction conditions conducted were the same as in Example 2. Crude 2,6-bis(4-aminophenoxy)pyridine thus obtained was recrystallized from ethanol to give 22.0 grams (75.1% yield) of pure product having a melting point of 152.5°–154.5° C.

EXAMPLE 7

In Example 1, 11.6 grams (0.215 mol) of sodium methoxide were used as a base, sulfolane was used as a solvent, and the reaction was carried out for 6 hours at a temperature of 170°–180° C. Other reaction procedures were the same as in Example 1. Crude product thus obtained was recrystallized from isopropyl alcohol to give 22.8 grams (77.8% yield) of pure 2,6-bis(3-aminophenoxy)pyridine having a melting point of 119°–120° C.

EXAMPLE 8

In Example 2, 11.6 grams (0.215 mol) of sodium methoxide were used as a base, sulfolane was used as a solvent, and the reaction was carried out for 8 hours at a temperature of 160°–170° C. Other reaction procedures were the same as in Example 2. Crude product thus obtained was recrystallized from ethanol to give 21.5 grams (73.4% yield) of pure 2,6-bis(4-aminophenoxy)-pyridine having a melting point of 152°–154° C.

EXAMPLE 9

In Example 3, 21.2 grams (0.2 mol) of anhydrous sodium carbonate were used as a base, 1-methyl-2-pyrrolidinone was used as a solvent, 0.3 gram of tris(3,6-dioxaheptyl)amine was added as a reaction accelerator, and the reaction was carried out for 12 hours at a temperature of 190°–200° C. Other reaction procedures conducted were the same as in Example 3.

2,6-Bis(3-aminophenoxy)pyridine thus obtained was 25.5 grams (87.0% yield) and had a melting point of 118°–119.5° C.

EXAMPLE 10

In Example 4, 21.2 grams (0.2 mol) of anhydrous sodium carbonate were used as a base, 1-methyl-2-pyrrolidinone was used as a solvent, 0.3 gram of tris(3,6-dioxaheptyl)amine was used as a reaction accelerator, and the reaction was carried out for 12 hours at a temperature of 180°–190° C. Other reaction procedures conducted were the same as in Example 4.

2,6-Bis(4-aminophenoxy)pyridine thus obtained was 25.5 grams (73.4% yield) and had a melting point of 152°–154° C.

EXAMPLE 11

A 200 ml flask equipped with a stirrer and a water separator was charged with 15.3 grams (0.11 mol) of 3-nitrophenol, 6.4 grams (0.11 mol) of flaked 96% potassium hydroxide, 100 ml of 1,3-dimethyl-2-imidazolidinone and 20 ml of benzene. Water in the reaction system was removed by the water separator under reflux of benzene.

In the next step, 7.4 grams (0.05 mol) of 2,6-dichloropyridine was added to the reaction mixture after lowering the internal temperature to 100° C. The temperature was raised again under ventilation of nitrogen and the internal temperature was maintained at 170°–175° C. The reaction was completed after conducting for 10 hours at this temperature. The resultant mixture was cooled and poured into 500 ml of water. The separated brown powder was filtered, washed with water and dried to give 16.3 grams (92.3% yield) of 2,6-bis(3-nitrophenoxy)pyridine. Crude 2,6-bis(3-nitrophenoxy)pyridine was recrystallized twice from ethanol to obtain pure product as pale brown needles having a melting point of 94°–96° C. The results of elementary analysis are as follows:

| Elementary analysis ($C_{17} H_{11} N_3 O_6$) | | | |
|---|---|---|---|
| | C | H | N |
| Calculated (%) | 57.79 | 3.14 | 11.89 |
| Found (%) | 57.36 | 3.32 | 11.79 |

In the next step, a sealed reaction vessel equipped with a stirrer and a thermometer was charged with 7.1 grams (0.02 mol) of above obtained 2,6-bis(3-nitrophenoxy)pyridine, 0.1 gram of 5% Pd/C catalyst and 25 ml of isopropyl alcohol. Hydrogen was introduced into the mixture with vigorous stirring. Reaction was carried out at 60°–70° C. for 4 hours, during which 2705 ml of hydrogen was absorbed. After completion of the reaction, the resultant mixture was immediately hot-filtered at the same temperature. The filtrate was added with 25 ml of water and allowed to cool. The separated white needles were filtered, washed and dried to give 5.2 grams (88.7% yield) of 2,6-bis(3-aminophenoxy)-pyridine having a melting point of 118.0°–119.5° C.

Results of elementary analysis are as follows.

| Elementary analysis ($C_{17} H_{11} N_3 O_6$) | | | |
|---|---|---|---|
| | C | H | N |
| Calculated (%) | 69.91 | 5.15 | 14.33 |
| Found (%) | 69.86 | 5.10 | 14.28 |

EXAMPLE 12

In Example 11, 100 ml of sulfolane was used as the solvent, 4.6 grams of 96% sodium hydroxide was used as the base, and the reaction was carried out for 8 hours at 180°–190° C.

Other reaction procedures were the same as in Example 11. Crude 2,6-bis(3-nitrophenoxy)pyridine thus obtained as the intermediate was 16.0 grams (90.6% yield).

A reaction vessel was charged with the above obtained intermediate, 0.1 gram of ferric chloride hexahydrate, 1 gram of active carbon and 25 ml of aqueous 70% 2-methoxyethanol solution. The mixture was warmed up to 85°–95° C. and added dropwise with 9 grams of hydrazine hydrate during 2 hours. The reactions was continued for 5 hours at the same temperature. After completing the reaction, the resultant mixture was filtered to remove the catalyst, added with 25 ml of water, and allowed to cool. The precipitated crystals were filtered, washed and dried to give 10.3 grams (70.3% overall yield) of 2,6-bis(3-aminophenoxy)pyridine having a melting point of 117.5°–119° C.

EXAMPLE 13

A reaction vessel equipped with a stirrer was charged with 15.3 grams (0.11 mol) of 3-nitrophenol, 11.9 grams (0.05 mol) of 2,6-dibromopyridine, 8.5 grams (0.08 mol) of anhydrous sodium carbonate and 100 ml of 1-methyl-2-pyrrolidinone. The mixture was elevated its temperature with stirring under ventilation of nitrogen and reacted at 160°–175° C. for 15 hours. After ending the reaction, the resultant mixture was treated by the same procedure as in Example 11 to give 16.5 grams (93.4% yield) of 2,6-bis(3-nitrophenoxy)pyridine as the intermediate.

The reducing reaction and post treatment of the intermediate was carried out in 35 ml of methanol in the presence of 0.3 gram of 5% platinum carbon catalyst by the same procedure as in Example 11. 2,6-Bis(3-aminophenoxy)pyridine thus obtained was 11.4 grams (77.8% overall yield) and had a melting point of 117.5°–119° C.

Reference Example 1

A reaction vessel equipped with a stirrer, reflux condenser and nitrogen inlet tube was charged with 29.3 grams (0.1 mol) of 2,6-bis(3-aminophenoxy)pyridine and 184.5 grams of N,N-dimethylacetamide. Under nitrogen atmosphere 31.2 grams (0.097 mol) of 3,3',4,4'-benzophenonetetracarboxylic dianhydride were added by portions at room temperature with care to prevent temperature rise of the solution above 30° C. and stirred for 20 hours at room temperature.

Polyamic acid thus obtained had an inherent viscosity of 0.52 dl/g measured at 35° C. in a solution of 0.5 gram of said polyamic acid in 100 ml of N,N-dimethylacetamide solvent.

A part of the polyamic acid solution was casted on a glass plate and heated for one hour each at 100° C., 200° C. and 300° C. to obtain a light-yellow transparent polyimide film. The polyimide film had a glass transition temperature of 206° C. in accordance with TMA penetration method, and 0.5% weight decrease temperature of 502° C. in accordance with DTA-TG.

Furthermore, the polyimide film was inserted between cold rolled steel panels (JIS 3141, spcc/SD, 25×100×1.6mm in dimension) which were preheated at 130° C. and pressed for 5 minutes at 320° C. with the pressure of 20 kg/cm². The bonded specimen had a lap shear strength of 330 kg/cm² at room temperature and 190 kg/cm² at 240° C. in accordance with JIS K-6848 and K-6850.

Reference example 2

A reaction vessel was charged with 7.325 grams (0.025 mol) of 2,6-bis(4-aminophenoxy)pyridine and 50 ml of N,N-dimethylacetamide. Under nitrogen atmosphere 7.894 grams (0.0245 mol) of 3,3',4,4'-benzophenonetetracarboxylic dianhydride were added by portions at room temperature with care to prevent the temperature rise of the solution and further stirred for 24 hours.

Polyamic acid thus obtained had an inherent viscosity of 0.63 dl/g.

A part of the polyamic acid solution was casted on a glass plate and heated for one hour each at 100° C., 200° C. and 300° C. to obtain a light-brown transparent tough film. The film had 0.5% weight decrease temperature of 503° C.

What we claim is:

1. 2,6-Bis(3- or 4-aminophenoxy)pyridine having the following formula (I):

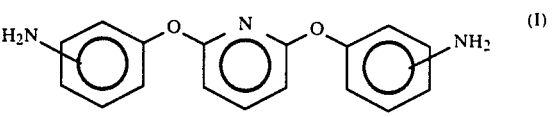

(where one amino group is located in each benzene ring either at both meta- or both para- position to each oxy radical).

* * * * *